United States Patent
Lee et al.

(10) Patent No.: US 12,122,766 B2
(45) Date of Patent: Oct. 22, 2024

(54) 3-AZABICYCLO[3,1,1]HEPTANE DERIVATIVE AND PHARMACEUTICAL COMPOSITION INCLUDING SAME

(71) Applicant: LG CHEM, LTD., Seoul (KR)

(72) Inventors: Sung Bae Lee, Daejeon (KR); Sang Yong Hong, Daejeon (KR); Suk Jun Youn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 802 days.

(21) Appl. No.: 17/280,353

(22) PCT Filed: Sep. 26, 2019

(86) PCT No.: PCT/KR2019/012522
§ 371 (c)(1),
(2) Date: Mar. 26, 2021

(87) PCT Pub. No.: WO2020/067735
PCT Pub. Date: Apr. 2, 2020

(65) Prior Publication Data
US 2022/0033381 A1 Feb. 3, 2022

(30) Foreign Application Priority Data
Sep. 27, 2018 (KR) .......................... 10-2018-0115191

(51) Int. Cl.
*C07D 403/06* (2006.01)
*C07D 403/04* (2006.01)

(52) U.S. Cl.
CPC ......... *C07D 403/06* (2013.01); *C07D 403/04* (2013.01)

(58) Field of Classification Search
CPC ............... C07D 403/06; C07D 403/04
See application file for complete search history.

(56) References Cited

U.S. PATENT DOCUMENTS

| | | | |
|---|---|---|---|
| 9,809,579 B2 | 11/2017 | Dowling et al. | |
| 2011/0263559 A1 | 10/2011 | Zhang et al. | |
| 2014/0336170 A1 | 11/2014 | Zhang et al. | |
| 2015/0203515 A1 | 7/2015 | Guckian et al. | |
| 2017/0174710 A1 | 6/2017 | Guckian et al. | |
| 2017/0183328 A1* | 6/2017 | Dowling | A61P 1/16 |
| 2017/0183342 A1 | 6/2017 | Bao et al. | |
| 2018/0037575 A1 | 2/2018 | Dowling et al. | |
| 2018/0133207 A1 | 5/2018 | Andrews et al. | |
| 2018/0134703 A1 | 5/2018 | Andrews et al. | |
| 2018/0148445 A1 | 5/2018 | Andrews et al. | |
| 2019/0062331 A1 | 2/2019 | Bao et al. | |
| 2019/0106412 A1 | 4/2019 | Dowling et al. | |
| 2019/0359623 A1 | 11/2019 | Ding et al. | |
| 2020/0030311 A1 | 1/2020 | Andrews et al. | |
| 2020/0148669 A1 | 5/2020 | Dowling et al. | |
| 2020/0377482 A1 | 12/2020 | Dowling et al. | |
| 2021/0309644 A1 | 10/2021 | Dowling et al. | |

FOREIGN PATENT DOCUMENTS

| | | |
|---|---|---|
| CN | 108473469 A | 8/2018 |
| JP | 2013-525370 A | 6/2013 |
| JP | 2015-528811 A | 10/2015 |
| KR | 10-2018-0083427 A | 7/2018 |
| WO | 2017-112719 A1 | 6/2017 |
| WO | 2017-115205 A1 | 7/2017 |
| WO | 2018-021977 A1 | 2/2018 |
| WO | 2018-071454 A1 | 4/2018 |
| WO | 2018-137593 A1 | 8/2018 |

OTHER PUBLICATIONS

Brooks WH, Guida WC, Daniel KG. The significance of chirality in drug design and development. Curr Top Med Chem. 2011;11(7): 760-70 (Year: 2011).*
Yirik, M.A., Sorokina, M. & Steinbeck, C. Maygen: an open-source chemical structure generator for constitutional isomers based on the orderly generation principle. J Cheminform 13, 48 (2021). (Year: 2021).*
Huard et al. (J. Med. Chem.2017, 60, 7835-7849). (Year: 2017).*
Horig et al. Journal of Translational Medicine 2004, 2(44) (Year: 2004).*
Schafer et al. Drug Discovery Today 2008, 13 (21/22), 913-916 (Year: 2008).*
Kentaro Futatsugi. J. Med. Chem. 2020, 63, 22, 13546-13560). (Year: 2020).*
Hannou et al. J. Clin. Invest. 2018; 128(2), 545-555 (Year: 2018).*
Extended European Search Report dated Jul. 19, 2021, issued in the corresponding European Patent Application No. 19864868.5, 6 pages.
International Search Report issued for International Application No. PCT/KR2019/012522 on Jan. 2, 2020, 8 pages.

* cited by examiner

*Primary Examiner* — Clinton A Brooks
*Assistant Examiner* — Jerica Katlynn Wilson
(74) *Attorney, Agent, or Firm* — ROTHWELL, FIGG, ERNST & MANBECK, P.C.

(57) ABSTRACT

The present invention relates to a compound of Formula 1, a pharmaceutically acceptable salt or isomer thereof, a pharmaceutical composition including the same, and a use. The compound of Formula 1 according to the present invention has ketohexokinase (KHK) inhibitory activity, and is effectively used for preventing or treating metabolic disease such as diabetes, diabetic complications, obesity, nonalcoholic fatty liver disease, and fatty hepatitis.

9 Claims, No Drawings

3-AZABICYCLO[3,1,1]HEPTANE DERIVATIVE AND PHARMACEUTICAL COMPOSITION INCLUDING SAME

CROSS-REFERENCE TO RELATED APPLICATIONS

This application is a 35 U.S.C. 371 National Phase Entry Application from PCT/KR2019/012522, filed on Sep. 26, 2019 and designating the United States, which claims the benefit of Korean Patent Application No. 10-2018-0115191, filed on Sep. 27, 2018, in the Korean Intellectual Property Office, the contents of which are incorporated herein by reference.

TECHNICAL FIELD

The present invention relates to a novel 3-azabicyclo[3,1,1]heptane derivative having ketohexokinase (KHK) inhibitory activity, and a pharmaceutical composition including the same as an active ingredient.

BACKGROUND OF THE INVENTION

The cause of nonalcoholic fatty liver disease which is one of metabolic diseases is widely known as the generation of a fatty liver, inflammation increase, apoptosis, etc. The nonalcoholic fatty liver disease is chronic disease and may progress to hepatic fibrillization, hepatocirrhosis, or hepatoma.

Meanwhile, ketohexokinase (KHK) is an enzyme involved in fructose metabolism and is a kind of kinase in charge of the phosphorylation of fructose during fructose metabolism. Different from glucose metabolism, fructose metabolism does not get energy dependent inhibition, and rapid hepatic accumulation of fat is induced to exert an influence on the generation of fatty liver. Accordingly, if the ketohexokinase (KHK) is inhibited, it is expected that the generation of fatty liver, which is one cause of nonalcoholic fatty liver disease, may be suppressed.

In an animal experimental model, it could be observed that overall indexes on metabolic diseases were improved through the inhibition of ketohexokinase (KHK) activity, and the phenotype of a ketohexokinase (KHK) knock out mouse did not show any difference from a normal mouse, and it could be expected that there are no major side effects due to ketohexokinase (KHK) inhibition.

However, considering that ketohexokinase (KHK) is in charge of phosphorylation using ATP, if the ketohexokinase (KHK) is inhibited, other kinds of kinase may be possibly inhibited, and accordingly, there has been a lot of concern about safety aspect as a medicine of chronic diseases. Accordingly, it is important that a ketohexokinase (KHK) inhibitor has selectivity with respect to another kinase.

Recently, research on ketohexokinase (KHK) is being actively conducted, but the development of a medicine useful for preventing and treating metabolic disease such as diabetes, diabetic complications, obesity, nonalcoholic fatty liver disease, fatty hepatitis, etc., is still required.

BRIEF SUMMARY OF THE INVENTION

The present invention provides a novel compound having ketohexokinase (KHK) inhibitory activity, and a pharmaceutically acceptable salt or isomer thereof.

In addition, the present invention provides a pharmaceutical composition for preventing or treating metabolic diseases, containing the compound as an active ingredient.

The present invention provides a compound of the following Formula (1), and a pharmaceutically acceptable salt or isomer thereof:

[Formula 1]

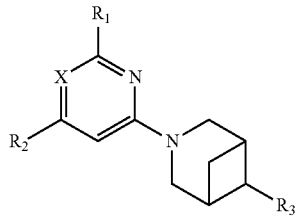

In Formula 1, $R_1$ represents a C3-C7 heterocycloalkyl containing N which is unsubstituted or substituted with C1-C3 alkyl, $R_2$ represents a C1-C3 alkyl which is unsubstituted or substituted with 1-5 halogen atoms, $R_3$ represents $-(CH_2)_m CO_2 H$, m is an integer of 0 to 2, and X represents N or C—CN.

In addition, the present invention provides a pharmaceutical composition for inhibiting ketohexokinase (KHK), including the compound, or the pharmaceutically acceptable salt or isomer thereof, as an active ingredient.

In addition, the present invention provides a pharmaceutical composition for preventing or treating metabolic disease, including the compound, or the pharmaceutically acceptable salt or isomer thereof, as an active ingredient.

Advantageous Effects

A 3-azabicyclo[3,1,1]heptane derivative compound of Formula 1 according to the present invention acts as a ketohexokinase (KHK) inhibitor and may be effectively used for preventing or treating metabolic disease such diabetes, diabetic complications, obesity, nonalcoholic fatty liver disease, and fatty hepatitis.

DETAILED DESCRIPTION OF THE INVENTION

Hereinafter, the present invention will be described in more detail to assist the understanding of the present invention. Here, it will be understood that words or terms used in the disclosure and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Hereinafter, the present invention will be explained in more detail referring to preparation embodiments and embodiments, but the scope of the present invention is not limited thereto.

The present invention provides a compound of Formula (1) below, and a pharmaceutically acceptable salt or isomer thereof.

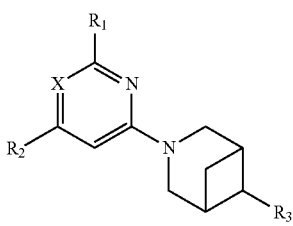

[Formula 1]

In Formula 1, $R_1$ represents a C3-C7 heterocycloalkyl containing N which is unsubstituted or substituted with C1-C3 alkyl, $R_2$ represents a C1-C3 alkyl which is unsubstituted or substituted with 1-5 halogen atoms, $R_3$ represents —$(CH_2)_m CO_2 H$, m is an integer of 0 to 2, and X represents N or C—CN.

The compound of Formula 1 according to the present invention may form a pharmaceutically acceptable salt. The pharmaceutically acceptable salt includes an acid addition salt formed from an acid forming a nontoxic acid addition containing pharmaceutically acceptable anion, for example, inorganic acid such as hydrochloric acid, sulfuric acid, nitric acid, phosphoric acid, hydrobromic acid, and hydroiodic acid, organic acid such as tartaric acid, formic acid, citric acid, acetic acid, trichloroacetic acid, trifluoroacetic acid, gluconic acid, benzoic acid, lactic acid, fumaric acid, maleic acid, and salicylic acid, sulfonic acid such as methanesulfonic acid, ethanesulfonic acid, benzenesulfonic acid, and p-toluenesulfonic acid, etc.

In addition, in a pharmaceutically acceptable carboxylate, for example, an alkali metal salt or alkaline earth metal salt formed by lithium, sodium, potassium, calcium, magnesium, etc., an amino acid salt such as lysine, arginine and guanidine, an organic salt such as dicyclohexylamine, N-methyl-D-glucamine, tris(hydroxymethyl) methylamine, diethanolamine, choline, and triethylamine, etc., are included. The compound of Formula 1 according to the present invention may be transformed into its salt by a common method.

The compound according to the present invention may have a chiral carbon center, and an asymmetric axis or asymmetric plane, and thus may be present as an E or Z isomer, a R or S isomer, a racemate, a partial stereoisomer mixture and individual stereoisomer, and all isomers and mixtures are included in the scope of the present invention.

Hereinafter, unless otherwise indicated for convenience, the compound of Formula 1 refers to all of the compound of Formula 1, the pharmaceutically acceptable salt thereof, and the isomer thereof.

In defining the compound of Formula 1, concepts defined as follow will be applied throughout. The definition below is applied to terms used individually or as a part of a larger group throughout the disclosure. The terms and abbreviations used in the disclosure have their original meanings unless otherwise defined.

"Heterocycloalkyl" means partially or wholly saturated hydrocarbon including one or more heteroatoms selected among N, O and S as a ring-forming atom and forming a single or fused ring, preferably, C3-C7 heterocycloalkyl containing N. For example, azetidinyl, pyrrolidinyl, piperidinyl, morpholinyl, imidazolinyl, piperazinyl, etc. are included, but is not limited thereto.

"Alkyl" means linear or branch chin-type hydrocarbon radical, preferably, linear or branched saturated hydrocarbon radical having 1 to 3 carbon atoms. Each carbon atom may be optionally substituted with one or more halogen atoms. For example, methyl, ethyl, n-propyl, i-propyl, trifluoromethyl, etc. are included, but is not limited thereto.

"Halogen" means a substituent selected from the group of fluoro, chloro, bromo and iodo. Besides, the terms and abbreviations used in the disclosure have their original meanings unless otherwise defined.

The typical compound of Formula 1 according to the present invention may include the compounds below, but is not limited thereto.

2-((1R,5S,6R)-3-(2-((S)-2-methylazetidine-1-yl)-6-(trifluoromethyl)pyrimidine-4-yl)-3-azabicyclo[3,1,1]heptane-6-yl)acetic acid;

2-((1R,5S,6S)-3-(2-((S)-2-methylazetidine-1-yl)-6-(trifluoromethyl)pyrimidine-4-yl)-3-azabicyclo[3,1,1]heptane-6-yl)acetic acid;

2-((1R,5S,6R)-3-(5-cyano-6-((S)-2-methylazetidine-1-yl)-4-(trifluoromethyl)pyridine-2-yl)-3-azabicyclo[3,1,1]heptane-6-yl)acetic acid;

2-((1R,5S,6S)-3-(5-cyano-6-((S)-2-methylazetidine-1-yl)-4-(trifluoromethyl)pyridine-2-yl)-3-azabicyclo[3,1,1]heptane-6-yl)acetic acid; and 2-((1R,5S,6R)-3-(5-cyano-6-(pyrrolidine-1-yl)-4-(trifluoromethyl)pyridine-2-yl)-3-azabicyclo[3,1,1]heptane-6-yl)acetic acid.

The compound of Formula 1, or the pharmaceutically acceptable salt or isomer thereof according to the present invention has effects as a ketohexokinase (KHK) inhibitor. Accordingly, the compound of Formula 1, or the pharmaceutically acceptable salt or isomer thereof according to the present invention is suitable for preventing or treating metabolic disease involving ketohexokinase (KHK).

In addition, the present invention provides a pharmaceutical composition for inhibiting ketohexokinase (KHK), including the compound of Formula 1, or the pharmaceutically acceptable salt or isomer thereof according to the present invention as an active ingredient. In addition, various types of prodrugs which may be transformed into the compound of Formula 1 in vivo according to purpose are included in the scope of the present invention.

The pharmaceutical composition according to the present invention may be used for preventing or treating metabolic disease involving ketohexokinase (KHK). The metabolic disease which may be prevented or treated by the pharmaceutical composition according to the present invention may include diabetes, diabetic complications, obesity, nonalcoholic fatty liver disease, fatty hepatitis, etc., but is not limited thereto, and preferably, the pharmaceutical composition may be used for preventing or treating nonalcoholic fatty liver disease.

In addition, the present invention provides a method for preparing a pharmaceutical composition for preventing or treating diabetes, diabetic complications, obesity, nonalcoholic fatty liver disease, or fatty hepatitis, including a step of mixing the compound of Formula 1, or the pharmaceutically acceptable salt or isomer thereof as an active ingredient with a pharmaceutically acceptable carrier.

The "pharmaceutical composition" may include the compound of the present invention, and other chemical components such as a diluent and a carrier. Accordingly, in the pharmaceutical composition, a pharmaceutically acceptable carrier, diluent, or excipient, or a combination thereof may be included as necessary. The pharmaceutical composition facilitates the administration of a compound to a living thing. The administration of a compound includes various techniques, and includes herein oral, injection, aerosol, parenteral, and local administration, but is not limited thereto.

The "carrier" means a compound for easy administration of the compound to a cell or tissue. For example, dimethylsulfoxide (DMSO) is a common carrier facilitating the administration of many organic compounds to the cell or tissue of a living thing.

The "diluent" is defined as a compound stabilizing the biologically active form of a target compound and diluted in water for dissolving the compound. A salt dissolved in a buffer solution is used as a diluent in the art. A commonly used buffer solution is a phosphate buffer saline solution imitating the salt type of a human body solution. Since a buffer salt may control the pH of a solution at a low concentration, a buffer diluent rarely deforms the biological activity of a compound.

The "pharmaceutically acceptable" means properties not damaging the biological activity and physical properties of a compound.

The compound of the present may be formulated into various pharmaceutical administration types on purpose. In case of preparing the pharmaceutical composition according to the present invention, an active ingredient, particularly, the compound of Formula 1, or the pharmaceutically acceptable slat or isomer thereof is mixed with various pharmaceutically acceptable carriers which may be selected according to the formulation to be prepared. For example, the pharmaceutical composition according to the present invention may be formulated into a medicine for injection, an oral medicine, etc.

The compound of the present invention may be formed into a medicine by a known method using a known carrier and excipient for medicine and put the medicine into a unit dosage type or various dosage vessels. The type of the medicine may include a solution in an oil or water medium, a suspension or emulsion type, and may include common dispersant, suspension agent or stabilizer. In addition, for example, a dry powder type which is used by dissolving in bacteria-free water from which a heating material is removed, may be included. The compound of the present invention may be also formulated into a suppository type using a common suppository base such as cocoa butter and other glycerides. A solid administration type for oral administration may include a capsule, a tablet, a pellet, a powder and a granule, and particularly, a capsule and a tablet are useful. The tablet and the pellet are preferably prepared as an enteric repellent. The solid administration type may be prepared by mixing the compound of the present invention with a carrier such as one or more inert diluents such as sucrose, lactose and starch, and a lubricant such as magnesium stearate, a disintegrating agent, a binder. The compound according to the present invention and the pharmaceutical composition containing the same may be administered in combination with another medicine, for example, another diabetes treating agent as necessary.

In addition, the present invention provides a method for preventing or treating metabolic disease involving ketohexokinase (KHK) in a mammal by administering the compound of Formula 1, or the pharmaceutically acceptable salt or isomer thereof as an active ingredient.

Typical examples for curing through a ketohexokinase (KHK) inhibitor may include metabolic disease such as diabetes, diabetic complications, obesity, nonalcoholic fatty liver disease, and fatty hepatitis, but is not limited thereto, and preferably, nonalcoholic fatty liver disease. In the present disclosure, the "treatment" means the suppression, delay or relief of the progress of a disease when used in an object showing the symptoms of a disease. The "prevention" means the suppression, delay or relief of the symptoms of a disease when used in an object not showing the symptoms of a disease but at higher risk.

The present invention also provides a method for preparing the compound of Formula 1. Hereinafter, explanation will be based on the preparation method of the compound of Formula 1 to assist the understanding of the present invention. However, a person skilled in the art would prepare the compound of Formula 1 by various methods based on the structure of Formula 1, and it should be interpreted that these methods are all included in the scope of the present invention. That is, the compound of Formula 1 may be prepared by optionally combining various synthetic methods described in the present disclosure or disclosed in prior arts, and these are considered to be included in the scope of the present invention. The preparation method of the compound of Formula 1 is not limited to the explanation below.

In preparing the compound of the present invention, reaction order may be appropriately changed. That is, an optional process may be performed in advance, an optional substituent changing process may be included, or an optional reagent may be used in addition to exemplified reagents as necessary. The compound obtained in each process may be separated or purified by common methods such as recrystallization, distillation, and silica gel column. In addition, a compound obtained in each process may be used in a subsequent process without separation or purification.

In the following reactions, unless otherwise indicated, all substituents are the same as defined above. Reagents and starting materials could be easily obtained on the market. Other materials may be prepared by the synthetic method of a known compound having similar structure, and by the synthetic methods described in the preparation examples and examples below. A compound used as a starting material of which preparation method is not specifically explained is a known compound or a compound which may be synthesized by a known method or a similar method as the known compound.

[Preparation Example 1] Preparation of methyl 2-(3-(2-chloro-6-(trifluoromethyl)pyrimidine-4-yl)-3-azabicyclo[3,1,1]heptane-6-yl)acetate

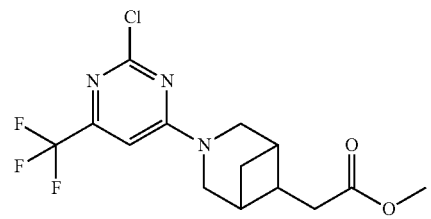 [SMILES: COC(=O)CC1C2CC1CN(c1cc(C(F)(F)F)nc(Cl)n1)C2]

The compound of Preparation Example 1 was prepared through steps A, B and C below.

(Step A) Preparation of Methyl 2-(3-benzyl-3-azabicyclo[3,1,1]heptane-6-ylidene)acetate

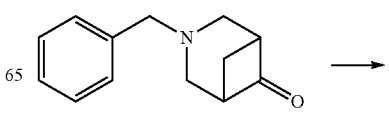

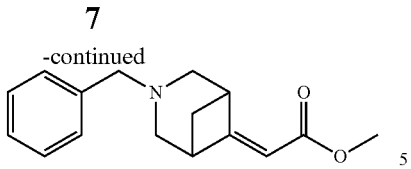

3-benzyl-3-azabicyclo[3,1,1]heptane-6-on (440 mg, 2.19 mmole), methyl 2-(dimethoxyphosphoryl)acetate (478 mg, 2.62 mmol) and sodium hydride (105 mg, 60%, 2.62 mmol) were dissolved in N,N'-dimethylformamide (30 ml), and sodium hydride (60 wt % in mineral oil, 105 mg, 2.62 mmol) was added thereto at 0° C., followed by stirring for 20 minutes and stirring at room temperature for 12 hours. The reaction solution was concentrated under a reduced pressure, water was added thereto, and the resultant product was extracted with ethyl acetate. An organic layer was washed with an aqueous sodium chloride solution, an aqueous sodium bicarbonate solution and water, dried with anhydrous magnesium sulfate, and filtered. The filtrate thus obtained was concentrated under a reduced pressure and then separated by column chromatography to obtain a compound of step A (440 mg, 1.71 mmol, 78%).

1H-NMR (500 MHz, CDCl3) δ 7.30-7.23 (m, 5H), 5.55 (s, 1H), 3.69 (s, 3H), 3.65 (d, 2H), 3.56 (m, 1H), 3.18-3.11 (m, 2H), 3.08-3.06 (dd, 1H), 2.93-2.89 (m, 2H), 2.01 (d, 1H), 1.90 (m, 1H)

(Step B) Preparation of Methyl 2-(3-azabicyclo[3,1,1]heptane-6-yl)acetate

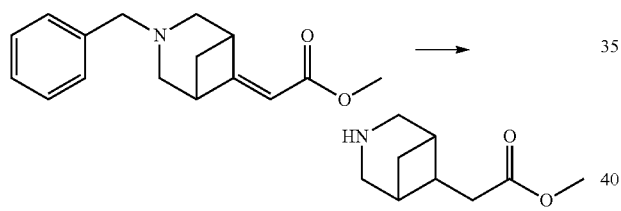

In a H-Cube reactor equipped with a Pd/C catalyst, methyl 2-(3-benzyl-3-azabicyclo[3,1,1]heptane-6-ylidene)acetate (440 mg, 1.71 mmol) obtained in the process of step A was dissolved in methanol (100 ml), and the reaction was performed under a hydrogen pressure of 5 atm at a reaction temperature of 50° C. for 3 hours to complete the reaction. The reaction solution was concentrated under a reduced pressure to obtain a compound of step B (240 mg, 1.42 mmol, 65%).

1H-NMR (500 MHz, CDCl3) δ 9.80 (br s, 2H), 3.69 and 3.68 (s, 3H), 3.68-3.50 (m, 4H), 2.71-2.48 (m, 4H), 2.31-2.21 (m, 2H), 2.03-1.91 (m, 1H)

(Step C) Preparation of Methyl 2-(3-(2-chloro-6-(trifluoromethyl)pyrimidine-4-yl)-3-azabicyclo[3,1,1]heptane-6-yl)acetate

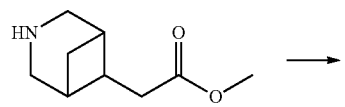

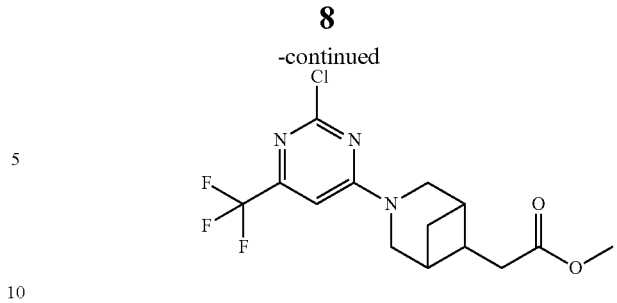

Methyl 2-(3-azabicyclo[3,1,1]heptane-6-yl)acetate (240 mg, 1.42 mmol) obtained in step B was dissolved in dichloromethane (50 ml), and 2,4-dichloro-6-(trifluoromethyl)pyrimidine (308 mg, 1.42 mmol) and diisopropylethylamine (0.74 ml, 4.25 mmol) were added thereto in order. After stirring at room temperature for 2 hours, an aqueous solution of 1 N hydrochloric acid was added to titrate to pH 2, and the resultant solution was extracted with ethyl acetate. An organic layer was washed with an aqueous sodium chloride solution, an aqueous sodium bicarbonate solution and water, dried with anhydrous magnesium sulfate, and filtered. The filtrate thus obtained was concentrated under a reduced pressure and then separated by column chromatography to obtain a compound of Preparation Example 1 (220 mg, 0.69 mmol, 48%).

1H-NMR (500 MHz, CDCl3) δ 6.67 and 6.66 (s, 1H), 3.93-3.58 (m, 7H), 2.73-2.62 (m, 3H), 2.50-2.10 (m, 3H), 1.47-1.42 (m, 1H)

[Preparation Example 2] Preparation of Methyl 2-((1R,5S,6R)-3-(2-((S)-2-methylazetidine-1-yl)-6-(trifluoromethyl)pyrimidine-4-yl)-3-azabicyclo[3,1,1]heptane-6-yl)acetate and methyl 2-((1R,5S,6S)-3-(2-((S)-2-methylazetidine-1-yl)-6-(trifluoromethyl)pyrimidine-4-yl)-3-azabicyclo[3,1,1]heptane-6-yl)acetate

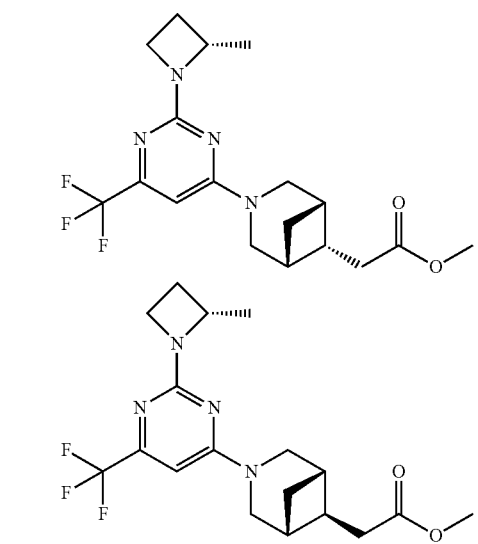

Methyl 2-(3-(2-chloro-6-(trifluoromethyl)pyrimidine-4-yl)-3-azabicyclo[3,1,1]heptane-6-yl)acetate (160 mg, 0.46 mmol) obtained in Preparation Example 1 was dissolved in dioxane (20 ml), and (S)-2-methylazetidine hydrochloride (98 mg, 0.92 mmol) and diisopropylethylamine (0.30 ml, 1.83 mmol) were added thereto in order. After stirring at 100° C. for 12 hours, an aqueous solution of 1 N hydrochloric acid was added to titrate to pH 2, and the resultant solution was extracted with ethyl acetate. An organic layer was washed with water and an aqueous sodium chloride solution, dried with anhydrous magnesium sulfate and filtered. The filtrate thus obtained was concentrated under a reduced pressure and separated by column chromatography to obtain methyl 2-((1R,5S,6R)-3-(2-((S)-2-methylazetidine-1-yl)-6-(trifluoromethyl)pyrimidine-4-yl)-3-azabicyclo[3,1,1]heptane-6-yl)acetate (100 mg, 0.26 mmol, 57%, a relatively less polar compound) and methyl 2-((1R,5S,6S)-3-(2-((S)-2-methylazetidine-1-yl)-6-(trifluoromethyl)pyrimidine-4-yl)-3-azabicyclo[3,1,1]heptane-6-yl)acetate (30 mg, 0.08 mmol, 17%, a relatively more polar compound).

Methyl 2-((1R,5S,6R)-3-(2-((S)-2-methylazetidine-1-yl)-6-(trifluoromethyl)pyrimidine-4-yl)-3-azabicyclo[3,1,1]heptane-6-yl)acetate: 1H-NMR (500 MHz, CDCl3) δ 6.09 (s, 1H), 4.46 (m, 1H), 4.02 (m, 1H), 3.96 (q, 1H), 3.82-3.60 (m, 2H), 3.67 (s, 1H), 3.51 (m, 2H), 2.65 (m, 1H), 2.58 (m, 2H), 2.36 (m, 1H), 2.29 (d, 2H), 2.13 (m, 1H), 1.93 (m, 1H), 1.41 (d, 3H), 1.43 (d, 1H)

Methyl 2-((1R,5S,6S)-3-(2-((S)-2-methylazetidine-1-yl)-6-(trifluoromethyl)pyrimidine-4-yl)-3-azabicyclo[3,1,1]heptane-6-yl)acetate: 1H-NMR (500 MHz, CDCl3) δ 6.09 (s, 1H), 4.45 (m, 1H), 4.05 (m, 1H), 3.95 (q, 1H), 3.84 (m, 2H), 3.68 (s, 3H), 3.61 (br s, 2H), 2.69 (d, 2H), 2.42 (m, 1H), 2.38 (m, 2H), 2.12 (m, 1H), 1.93 (m, 1H), 1.05 (d, 3H). 1.42 (m, 1H)

[Preparation Example 3] Preparation of Methyl 2-(3-(6-chloro-5-cyano-4-(trifluoromethyl)pyridine-2-yl-3-azabicyclo[3,1,1]heptane-6-yl)acetate

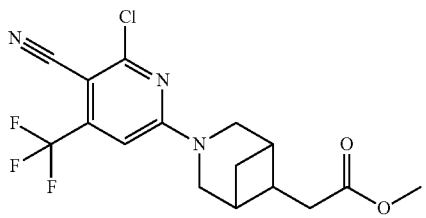 [SMILES: COC(=O)CC1C2CC1CN(c1cc(C(F)(F)F)c(C#N)c(Cl)n1)C2]

Methyl 2-(3-azabicyclo[3,1,1]heptane-6-yl)acetate (98 mg, 0.58 mmol) obtained in step B of Preparation Example 1 was dissolved in dichloromethane (50 ml), and 2,6-dichloro-4-(trifluoromethyl)nicotinitrile (140 mg, 0.58 mmol) and diisopropylethylamine (0.4 ml, 2.32 mmol) were added thereto in order. After stirring at room temperature for 2 hours, an aqueous solution of 1 N hydrochloric acid was added to titrate to pH 2, and the resultant solution was extracted with ethyl acetate. An organic layer was washed with an aqueous sodium chloride solution, an aqueous sodium bicarbonate solution and water, dried with anhydrous magnesium sulfate, and filtered. The filtrate thus obtained was concentrated under a reduced pressure and then separated by column chromatography to obtain a compound of Preparation Example 3 (150 mg, 0.40 mmol, 69%).

1H-NMR (500 MHz, CDCl3) δ 6.71 (d, 1H), 3.93-3.62 (m, 7H), 2.74-2.20 (m, 6H), 1.50-1.48 (m, 1H)

[Preparation Example 4] Preparation of Methyl 2-(3-(5-cyano-6-((S)-2-methylazetidine-1-yl)-4-(trifluoromethyl)pyridine-2-yl)-3-azabicyclo[3,1,1]heptane-6-yl)acetate

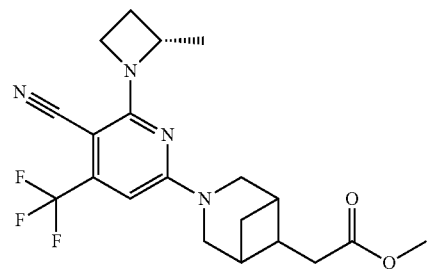 [SMILES: COC(=O)CC1C2CC1CN(c1cc(C(F)(F)F)c(C#N)c(N3CC[C@@H]3C)n1)C2]

A compound of Preparation Example 4 (95 mg, 0.23 mmol, 63%) was obtained by the same method as in Preparation Example 2 using methyl 2-(3-(6-chloro-5-cyano-4-(trifluoromethyl)pyridine-2-yl)-3-azabicyclo[3,1,1]heptane-6-yl)acetate (140 mg, 0.37 mmol) obtained in Preparation Example 3.

1H-NMR (500 MHz, CDCl3) δ 6.16 (s, 1H), 4.67 (m, 1H), 4.53 (m, 1H), 4.16 (m, 1H), 3.92-3.57 (m, 7H), 2.72-2.32 (m, 6H), 2.17 (m, 1H), 2.05 (m, 1H), 1.52 (d, 3H), 1.45 (m, 1H)

[Example 1] 2-((1R,5S,6R)-3-(2-((S)-2-methylazetidine-1-yl)-6-(trifluoromethyl)pyrimidine-4-yl)-3-azabicyclo[3,1,1]heptane-6-yl)acetic Acid

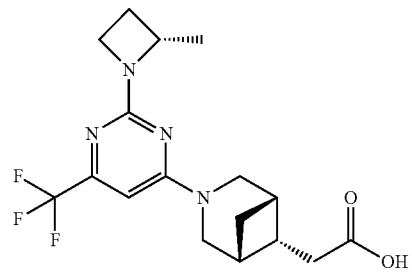 [SMILES: C[C@H]1CCN1c1nc(N2C[C@H]3C[C@@H](C2)[C@H]3CC(=O)O)cc(C(F)(F)F)n1]

Methyl 2-((1R,5S,6R)-3-(2-((S)-2-methylazetidine-1-yl)-6-(trifluoromethyl)pyrimidine-4-yl)-3-azabicyclo[3,1,1]heptane-6-yl)acetate (100 mg, 0.26 mmol) obtained in Preparation Example 2 and lithium hydroxide (25 mg, 1.04 mmol) were dissolved in water (1 ml) and tetrahydrofuran (4 ml), and stirred at room temperature for 24 hours. Then, an aqueous solution of 1 N hydrochloric acid was added thereto to titrate to pH 2, and the resultant solution was extracted with ethyl acetate. An organic layer was washed with an aqueous sodium chloride solution, dried with anhydrous magnesium sulfate and filtered. The filtrate thus obtained was concentrated under a reduced pressure and separated by column chromatography to obtain a compound of Example 1 (86 mg, 0.23 mmol, 89%).

1H-NMR (500 MHz, CDCl3) δ 6.13 (s, 1H), 4.48 (m, 1H), 4.08 (m, 1H), 3.96 (q, 1H), 3.87-3.65 (m, 2H), 3.55 (m, 2H), 2.69 (m, 1H), 2.64 (m, 2H), 2.42 (m, 1H), 2.37 (d, 2H), 2.16 (m, 1H), 1.97 (m, 1H), 1.54 (d, 3H), 1.46 (d, 1H)

[Example 2] 2-((1R,5S,6S)-3-(2-((S)-2-methylazetidine-1-yl)-6-(trifluoromethyl)pyrimidine-4-yl)-3-azabicyclo[3,1,1]heptane-6-yl)acetic Acid

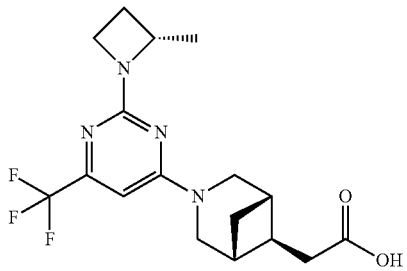 [SMILES: C[C@H]1CCN1c1nc(N2C[C@H]3C[C@@H](C2)[C@@H]3CC(=O)O)cc(C(F)(F)F)n1]

2-((1R,5S,6S)-3-(2-((S)-2-methylazetidine-1-yl)-6-(trifluoromethyl)pyrimidine-4-yl)-3-azabicyclo[3,1,1]heptane-6-yl)acetate (30 mg, 0.08 mmol) obtained in Preparation Example 2 and lithium hydroxide (8 mg, 0.31 mmol) were dissolved in water (1 ml) and tetrahydrofuran (4 ml), and stirred at room temperature for 24 hours. Then, an aqueous solution of 1 N hydrochloric acid was added thereto to titrate to pH 2, and the resultant solution was extracted with ethyl acetate. An organic layer was washed with an aqueous sodium chloride solution, dried with anhydrous magnesium sulfate and filtered. The filtrate thus obtained was concentrated under a reduced pressure and separated by column chromatography to obtain a compound of Example 2 (25 mg, 0.08 mmol, 86%).

1H-NMR (500 MHz, CDCl3) δ 6.13 (s, 1H), 4.48 (m, 1H), 4.08 (m, 1H), 4.01 (q, 1H), 3.99 (m, 2H), 3.67 (br s, 2H), 2.76 (d, 2H), 2.47 (m, 1H), 2.40 (m, 2H), 2.15 (m, 1H), 1.98 (m, 1H), 1.52 (d, 3H), 1.45 (m, 1H)

[Example 3] 2-((1R,5S,6R)-3-(5-cyano-6-((S)-2-methylazetidine-1-yl)-4-(trifluoromethyl)pyridine-2-yl)-3-azabicyclo[3,1,1]heptane-6-yl)acetic Acid

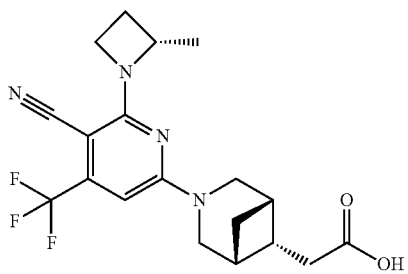 [SMILES: C[C@H]1CCN1c1nc(N2C[C@H]3C[C@@H](C2)[C@H]3CC(=O)O)cc(C(F)(F)F)c1C#N]

A compound of Example 3 (42 mg, 0.11 mmol, 48%, a relatively less polar compound) was obtained by the method of Example 1 using 2-(3-(5-cyano-6-((S)-2-methylazetidine-1-yl)-4-(trifluoromethyl)pyridine-2-yl)-3-azabicyclo[3,1,1]heptane-6-yl)acetate (95 mg, 0.23 mmol) obtained in Preparation Example 4.

1H-NMR (500 MHz, CDCl3) δ 6.17 (s, 1H), 4.70 (m, 1H), 4.55 (m, 1H), 4.19 (m, 1H), 3.91-3.63 (m, 4H), 2.70 (m, 3H), 2.37 (m, 2H), 2.18 (m, 1H), 2.00 (m, 1H), 1.52 (d, 3H), 1.45 (d, 1H)

[Example 4] 2-((1R,5S,6S)-3-(5-cyano-6-((S)-2-methylazetidine-1-yl)-4-(trifluoromethyl)pyridine-2-yl)-3-azabicyclo[3,1,1]heptane-6-yl)acetic Acid

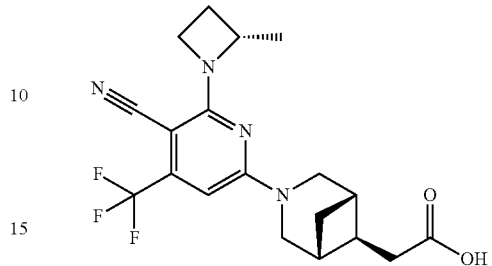

A compound of Example 4 (37 mg, 39%, a relatively more polar compound) was obtained by the method of Example 1 using 2-(3-(5-cyano-6-((S)-2-methylazetidine-1-yl)-4-(trifluoromethyl)pyridine-2-yl)-3-azabicyclo[3,1,1]heptane-6-yl)acetate obtained in Preparation Example 4.

1H-NMR (500 MHz, CDCl3) δ 6.15 (s, 1H), 4.69 (m, 1H), 4.54 (m, 1H), 4.18 (m, 1H), 3.94-3.67 (m, 4H), 2.76 (m, 2H), 2.44 (m, 4H), 2.14 (m, 1H), 2.00 (m, 1H), 1.52 (d, 3H), 1.46 (m, 1H)

[Example 5] 2-((1R,5S,6R)-3-(5-cyano-6-(pyrrolidine-1-yl)-4-(trifluoromethyl)pyridine-2-yl)-3-azabicyclo[3,1,1]heptane-6-yl)acetic Acid

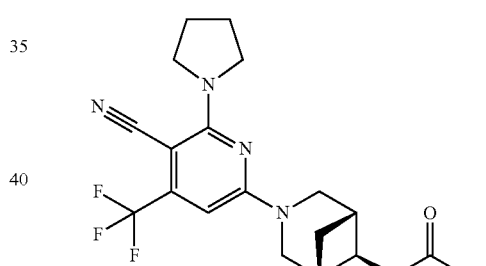

A compound of Example 5 (12 mg, 32%) was obtained by applying the methods of Preparation Example 4 and Example 4 in order except for using methyl 2-(3-(6-chloro-5-cyano-4-(trifluoromethyl)pyridine-2-yl)-3-azabicyclo[3,1,1]heptane-6-yl)acetate (35 mg, 0.094 mmol) obtained in Preparation Example 3, and pyrrolidine instead of (S)-2-methylazetidinehydrochloride.

1H-NMR (500 MHz, CDCl3) δ 6.17 (s, 1H), 3.88 (m, 2H), 3.80 (m, 4H), 3.70 (br S, 2H), 2.77 (d, 2H), 2.45 (m, 3H), 2.16 (m, 1H), 1.96 (m, 4H), 1.46 (m, 1H)

[Experimental Example] Activity Measurement of Ketohexokinase Inhibitor In Vitro Ketohexokinase (KHK) was expressed in *E. coli*, and was purified using His tag. In order to measure the activity of the purified KHK, Transcreener ADP2 TR-FRET Red Assay kit of BellBrook Labs was used. A method of measuring the amount of ADP produced using TR-FRET after reacting a solution including appropriate concentrations of a KHK protein, ATP, and fructose for 15 minutes, was used. In order to observe the activity of a ketohexokinase (KHK) inhibitor, ketohexokinase (KHK) and an inhibitor with an appropriate concentration were reacted first for 30 minutes, and then, reacted with a solution include a substrate of ketohexokinase (KHK) for 15 minutes. Then, reaction for TR-FRET was conducted for 1 hour, and fluorescence was measured using Envision apparatus of PerkinElmer Co. The predetermined value of Envision apparatus was determined according to the optimization process of TR-FRET published by BellBrook Lab.

The resultant value for each concentration of the ketohexokinase (KHK) inhibitor is determined by a ratio of 665 nm wavelength and 615 nm wavelength. IC50 is analyzed by measuring the 665/615 ratio value with respect to the concentration of each inhibitor and using a statistics software (Prizm). IC50 was represented by the concentration of the inhibitor, showing 50% of the maximum inhibition activity by the inhibitor.

IC50 of Example compounds obtained through the experiment are shown in Table 1 below

A≥10 μM, B≥1 μM, C=1-0.2 μM, D≤21.2 μM

TABLE 1

|  | Example 1 | Example 2 | Example 3 | Example 4 | Example 5 |
|---|---|---|---|---|---|
| IC50 | B | D | B | D | D |

The invention claimed is:

1. A compound of the following Formula 1, or a pharmaceutically acceptable salt or stereoisomer thereof:

[Formula 1]

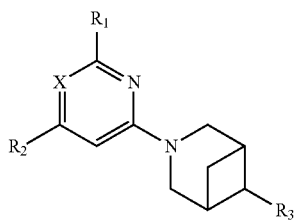

in the Formula 1,
R₁ is a C3-C7 heterocycloalkyl containing N which is unsubstituted or substituted with C1-C3 alkyl,
R₂ is a C1-C3 alkyl which is unsubstituted or substituted with 1-5 halogen atoms,
R₃ represents —(CH₂)$_m$CO₂H,
m is an integer of 0 to 2, and
X represents N or C—CN.

2. The compound, or the pharmaceutically acceptable salt or stereoisomer thereof according to claim 1, wherein the compound is selected from the following group:
   2-((1R,5S,6R)-3-(2-((S)-2-methylazetidine-1-yl)-6-(trifluoromethyl)pyrimidine-4-yl)-3-azabicyclo[3,1,1]heptane-6-yl)acetic acid;
   2-((1R,5S,6S)-3-(2-((S)-2-methylazetidine-1-yl)-6-(trifluoromethyl)pyrimidine-4-yl)-3-azabicyclo[3,1,1]heptane-6-yl)acetic acid;
   2-((1R,5S,6R)-3-(5-cyano-6-((S)-2-methylazetidine-1-yl)-4-(trifluoromethyl)pyridine-2-yl)-3-azabicyclo[3,1,1]heptane-6-yl)acetic acid;
   2-((1R,5S,6S)-3-(5-cyano-6-((S)-2-methylazetidine-1-yl)-4-(trifluoromethyl)pyridine-2-yl)-3-azabicyclo[3,1,1]heptane-6-yl)acetic acid; and
   2-((1R,5S,6R)-3-(5-cyano-6-(pyrrolidine-1-yl)-4-(trifluoromethyl)pyridine-2-yl)-3-azabicyclo[3,1,1]heptane-6-yl)acetic acid.

3. The compound, or the pharmaceutically acceptable salt or stereoisomer thereof according to claim 1, which has a ketohexokinase (KHK) inhibiting activity.

4. A pharmaceutical composition for inhibiting ketohexokinase (KHK), or preventing or treating metabolic disease comprising the compound, or the pharmaceutically acceptable salt or stereoisomer thereof according to claim 1, as an active ingredient and a pharmaceutically acceptable carrier.

5. The pharmaceutical composition for preventing or treating metabolic disease according to claim 4, wherein the metabolic disease is diabetes, diabetic complications, obesity, nonalcoholic fatty liver disease, or fatty hepatitis.

6. The pharmaceutical composition for preventing or treating metabolic disease according to claim 4, wherein the metabolic disease is nonalcoholic fatty liver disease.

7. A method for treating metabolic disease in a mammal, comprising administering to the mammal in need thereof the compound, or the pharmaceutically acceptable salt or stereoisomer thereof according to claim 1.

8. The method of claim 7, wherein the metabolic disease is diabetes, diabetic complications, obesity, nonalcoholic fatty liver disease, or fatty hepatitis.

9. The method of claim 7, wherein the metabolic disease is nonalcoholic fatty liver disease.

* * * * *